United States Patent [19]
Wertz

[11] Patent Number: 5,493,221
[45] Date of Patent: Feb. 20, 1996

[54] METHOD AND APPARATUS FOR DETECTING WELD JUNCTIONS IN STEEL SHEETS USING AN INDUCTIVE SENSOR TO DETECT THICKNESS VARIATIONS IN THE SHEET

[75] Inventor: Ronald D. Wertz, Boulder, Colo.

[73] Assignee: Alltrista Corporation, Muncie, Ind.

[21] Appl. No.: 72,465

[22] Filed: Jun. 4, 1993

[51] Int. Cl.$^6$ .............................. G01B 7/06; G01R 33/12; G01N 27/72
[52] U.S. Cl. .......................................... 324/229; 324/234
[58] Field of Search ................................. 324/229, 230, 324/231, 207.26, 226, 262, 236, 239, 234; 271/262; 340/676

[56] References Cited

U.S. PATENT DOCUMENTS

| | | | |
|---|---|---|---|
| 3,600,672 | 8/1971 | Kubo et al. | 324/209 |
| 3,833,850 | 9/1974 | Weber | 324/236 |
| 3,880,749 | 4/1975 | Ramsay | 340/676 |
| 4,879,513 | 11/1989 | Spiegel et al. | 271/262 |

Primary Examiner—Walter E. Snow
Attorney, Agent, or Firm—Willian Brinks Hofer Gilson & Lione

[57] ABSTRACT

Apparatus (40) locates welds or other junctures (20) in sheet material (12). The apparatus (40) includes a sensor (16) that produces a varying signal that is a function of the distance (100) between a surface (26) of sheet material (12) and the sensor (16), a differentiator circuit (42) differentiates the varying signal as a function of time, a comparator (44) compares the differentiated signal with a calculated allowable and sends a signal to an input (90) of an electronic latch (46), the electronic latch (46) sends a signal to a reject mechanism (48), and the reject mechanism (48) sends a reject-accomplished signal to a reset terminal (98) of the electronic latch (46). The method of the invention includes transporting the sheet material (12), producing a rate of change signal that is a function of changes in thickness (18) of the sheet material (12), determining an allowable rate of change signal, and comparing the produced rate of change signal with the allowable rate of change signal. Preferably, the producing step includes obtaining a varying electrical signal whose variations are a function of variations in the thickness (18) of the sheet material (12), and developing a rate of change of signal from the varying electrical signal.

15 Claims, 1 Drawing Sheet

METHOD AND APPARATUS FOR DETECTING WELD JUNCTIONS IN STEEL SHEETS USING AN INDUCTIVE SENSOR TO DETECT THICKNESS VARIATIONS IN THE SHEET

BACKGROUND OF THE INVENTION

1. Field of the Invention

The present invention relates generally to detecting welds or junctures in sheets or strips of material. More particularly, the present invention relates to apparatus and method for detecting welds in steel sheets or strips.

2. Description of the Related Art

In the manufacture of steel strips, steel sheets, and other metallic and nonmetallic strips and sheets, it is common to weld or join two pieces of strip or sheet together. While subsequent processing, such as hot or cold rolling of steel strips or steel sheets, may obscure welds, there remains changes in thickness at the weld or juncture that are detrimental to the production of uniform products.

More particularly, a thickened area at a weld or juncture often results in irregular drawing or even fracturing of a part that is being deep drawn. The problem of thickened areas at welds or junctures becomes particularly critical when a sheet being drawn has additional costs, such as plating or decorating, invested in previous operations on the sheet to be drawn.

The prior art has addressed the problem of detecting flaws or imperfections in strips and sheets. A number of prior art patents have been directed to the use of eddy currents to detect weld seams. An early example of this type of prior art is Harmon, U.S. Pat. No. 2,832,040.

Detecting of weld seams has been accomplished by measuring thicknesses of sheets or strips, that is by measuring changes in thicknesses. An early device that used eddy currents for measuring thicknesses of sheets is taught by Lenehan in U.S. Pat. No. 2,443,661: and continuing development in the art is seen in Charpentier, U.S. Pat. No. 4,757,259 and Lonchampt et al., U.S. Pat. No. 4,727,322.

Not only have eddy current devices been used to detect weld seams, but also they have been used to detect various flaws. One such device is taught by Mandula, Jr., et al. In U.S. Pat. No. 3,263,809; and another is taught by Harmon in U.S. Pat. No. 3,497,799.

However, changes in thicknesses of sheets or strips at welds or junctures are relatively small, especially for sheets or strips with gauges having thicknesses in the range of 0.006 to 0.010 inches (0.152 to 0.254 millimeters). Thus variations in the output of position sensors, or thickness sensors, have been relatively small; so that, even with amplification, it has been difficult to accurately sense weld seams. This has been an especially difficult problem because of the fact that seam-weld detection is typically accomplished with sheet or strip velocities in the order of 600 feet per minute (3.048 meters/second).

SUMMARY OF THE INVENTION

In the present invention, determining the rate of change of thickness of a sheet or strip is used to overcome the problem of measuring small changes in thicknesses of rapidly moving sheets or strips, and then determining whether these small changes represent welds, seams, or junctures.

That is, since variations of thickness extend for a relatively small longitudinal distance, a change in thickness of 0.0015 inches (0.0381 millimeters) over a longitudinal distance of 0.125 inches (3.175 millimeters) represents a rate of change of thickness of 1.44 inches per second (36.576 min./sec.).

The method of the present invention includes transporting sheet material, producing a rate of change signal that is a function of changes in thickness of the sheet material, determining an allowable rate of change signal, and comparing the produced rate of change signal with the allowable rate of change signal.

Preferably, the step of producing a rate of change signal includes obtaining a varying electrical signal whose variations are a function of variations in the thickness of the sheet material, and differentiating the rate of change of the varying signal as a function of time.

It is an object of the present invention to provide apparatus and method for measuring changes in thicknesses of sheets or strips.

It is a further object of the present invention to provide apparatus and method in which welds or junctures are detected in sheets or strips that are being transported rapidly.

In a first aspect of the present invention, a method is provided for detecting junctures in a sheet material, which method comprises transporting the sheet material; producing a rate of change signal that is a function of changes in the thickness of the sheet material; determining an allowable rate of change signal; and comparing the produced rate of change signal with the allowable rate of change signal.

In a second aspect of the present invention, a method is provided for detecting junctures in a sheet material, which method comprises transporting the sheet material at a given velocity; obtaining a varying electrical signal whose variations are a function of variations in the thickness of the sheet material; and developing a rate of change signal by differentiating the varying electrical signal as a function of time.

In a third aspect of the present invention, apparatus is provided for detecting a juncture in a sheet material that is being transported at a given velocity, which apparatus comprises means for producing a rate of change signal that is a function of changes in thickness of the sheet material and the given velocity; and means, including a comparator that is operatively connected to the producing means, for comparing the rate of change signal with a calculated allowable.

In a fourth aspect of the present invention, apparatus is provided for detecting a juncture in a sheet material that is being transported at a given velocity, which apparatus comprises means, including a sensor, for producing a varying signal that is a function or changes in thickness of the sheet material and the given velocity; means, being operatively connected to the sensor, for differentiating the varying signal as a function of time; and means, including a comparator that is operatively connected to the differentiating means, for comparing the differentiated signal with an allowable value.

DESCRIPTION OF THE PREFERRED EMBODIMENTS

Figure 1:
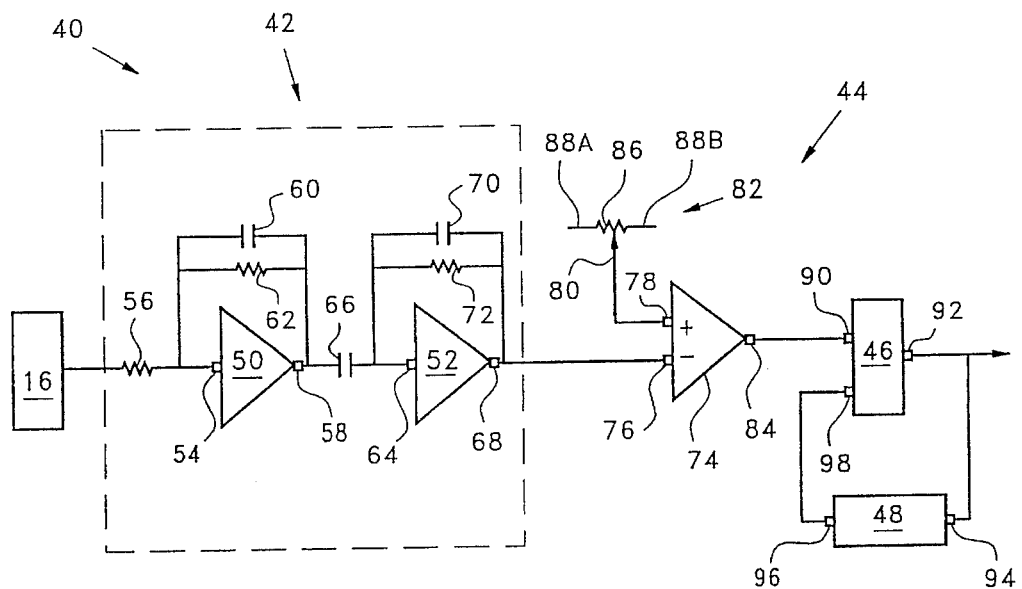
FIG. 1 is a schematic drawing of a preferred embodiment of the present invention, including the sensor, the differentiator circuit, the comparator, the electronic latch with reset, and a schematic representation of a mechanical reject mechanism.
Figure 2:
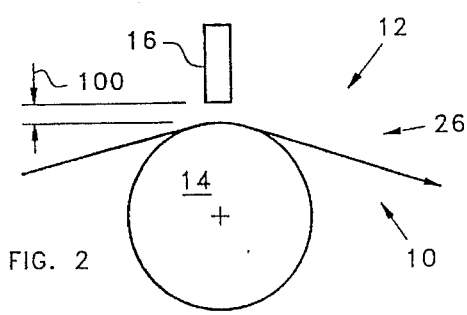
FIG. 2 is a schematic representation showing the front elevation of a supporting roller, the sensor of FIG. 1, and an edge of a steel strip that is being supported by the supporting roller, and that is passing between the supporting roller and the sensor.
Figure 3:
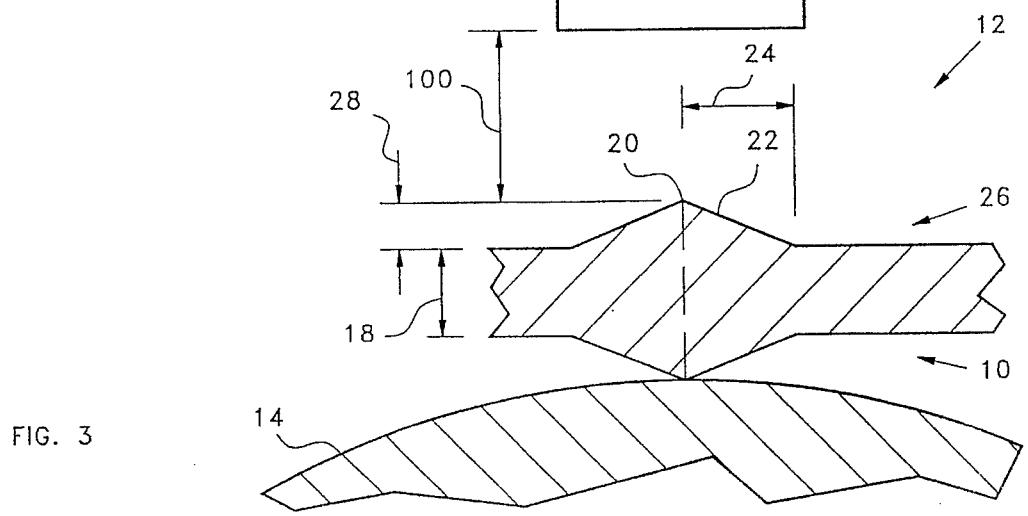
FIG. 3 is a greatly enlarged cross-section of a strip, showing the increase in thickness of the strip at a weld or juncture thereof.

Referring to FIGS. 1–3, but particularly to FIG. 2, a first side 10 of a sheet material 12 is supported on a support roller 14 of FIG. 2 and is transported between the support roller 14 and a sensor 16 by any suitable mechanism, not an inventive part of the present invention. Typically, the sheet material 12 is transported at relatively high velocities, such as 600 feet per minute (3.048 meters/sec.) by apparatus, not shown, not an inventive part of the present invention.

Referring now to FIG. 3, the sheet material 12 has a sheet thickness 18 that may be of any gauge of hot rolled steel, cold rolled steel, other ferrous and nonferrous materials, or nonmetallic material. Further, the term "sheet material" 12 is used herein to refer to any material which is elongated with respect to the thickness thereof, and which may include welds or junctures. Thus, various shapes such as bars, rods, and rolled shapes are included in the general classification of sheet materials 12.

The sheet material 12 includes a weld, or juncture, 20 in which a thickened portion, or juncture area, 22 at the weld 20 extends longitudinally each way from the weld 20 by a longitudinal length 24; and the thickened portion 22 extends outwardly from a second side, or surface, 26 of the sheet material 12 by a thickness increase 28.

Typically, the apparatus and method of the present invention are used to detect welds 20 in sheet material 12 having thicknesses 18 in the range of 0.006 to 0.010 inches (0.152 to 0.254 millimeters). With sheet material 12 in this range of thickness 18, the thickened portion 22 may have a thickness increase 28 of 0.0015 inches (0.0381 millimeters) from the second side 26, and may have a longitudinal length 24 of 0.125 inches (3.175 millimeters) from the weld 20.

Therefore, with a thickness increase 28 of 0.0015 inches (0.0381 occurring in the longitudinal length 24 of 0.125 inches (3.175 mm), and a transporting velocity of 600 feet/minute (3.048 meters/sec), and assuming a linear change in the thickness 18 as shown in FIG. 3, the rate of change in the thickness 18 is 1.44 inches/second (36.576 mm/sec).

Referring now to FIGS. 1 and 3, apparatus 40 for detecting a weld 20 in the sheet material 12 includes the sensor 16, a differentiator circuit 42, a comparator 44, an electronic latch 46, and a reject mechanism 48.

The sensor 16 is of the inductive, or variable impedance, type. A suitable transducer for use in the present invention is in the KD-2300/2310 series manufactured by Kaman Instrumentation Corp., Measuring Systems Group, Department M. Box 7463, Colorado Springs, Col. 80933. More particularly, the sensitivity, range, and stability of sensor KD-2300-8C makes it especially suitable for use in the present invention. This particular sensor is usable for measuring the distance from the sensor to both magnetic and nonmagnetic materials.

The differentiator circuit 42 includes a first operational amplifier 60 and a second operational amplifier 52. The first operational amplifier 50 includes an input 54 that is operatively connected to the sensor 16 by a coupling resistor 56, and an output 58. Feedback from the output 58 of the first operational amplifier 50 to the input 64 thereof is provided by a feedback capacitor 60 having a capacitance of 1.0 picofarads, and by a feedback resistor 62 having a resistance of 100,000 ohms.

The first operational amplifier 50 provides amplification for a variable signal that it receives from the sensor 16; the feedback resistor 62 cooperates with the coupling resistor 56 to determine the signal gain from the input 54 to the output 58; and the feedback capacitor 60 provides noise filtering.

The output 58 of the first operational amplifier 50 is operatively connected to an input 64 of the second operational amplifier 52 by a coupling capacitor 66 having a capacitance of 0.47 microfarad. Feedback from an output 68 of the second operational amplifier 52 to the input 64 thereof is provided by a feedback capacitor 70 having a capacitance of 0.2 picofarads, and by a feedback resistor 72 having a resistance of 400,000 ohms. The second operational amplifier 52 differentiates the amplified and variable signal that is provided to the input 64 thereof by the sensor 16 and the first operational amplifier 50.

The comparator 44 includes a third operational amplifier 74 having a negative input 76 that is directly coupled to the output 68 of the second operational amplifier 52, a positive input, or reference input, 78 that is connected to a wiper 80 of a potentiometer 82, and an output 84. The potentiometer 82 includes a resistance 86 which has ends, 88A and 88B, which are connected to 15 volt plus and minus voltage sources, not shown, not an inventive part of the present invention.

The output 84 of the third operational amplifier 74 is connected to an input 90 of the electronic latch 46, an output 92 of the electronic latch 46 is connected to an input 94 of the reject mechanism 48, and a reject-accomplished output 96 of the reject mechanism 48 is connected to a reset terminal 98 of the electronic latch 46. The reject mechanism 48 is shown symbolically and the particular construction of the reject mechanism 48 is not an inventive part of the present invention.

In summary, apparatus 40 for detecting the juncture 20 in the sheet material 12, that is being transported at a given velocity, includes means, comprising both the sensor 16 and the differentiator circuit 42, for producing a rate of change signal that is a function of changes in the thickness 18 of the sheet material 12 and the velocity at which the sheet material 12 is being transported. The apparatus 40 further includes means, comprising the comparator 44 that is operatively connected to the producing means, 16 and 42, for comparing the rate of change signal with a calculated allowable rate of change signal by positioning the wiper 80 of the potentiometer 82.

The method of the present invention includes transporting sheet material 12, producing a rate of change signal that is a function of changes in the thickness 18 of the sheet material 12 by the use of the sensor 16 and the differentiator circuit 42, determining an allowable rate of change signal and using the potentiometer 82 to apply this allowable rate of change signal to the comparator 44, and using the comparator 44 to compare the produced rate of change signal with the allowable rate of change signal.

Referring to FIG. 3, the sensor 16 measures a distance 100 between the sensor 16 and the second side 26 of the sheet material 12. The support roller 14 supports the first side 10 and transports the sheet material 12 past the sensor 16 which dynamically measures the distance 100 as a function of the thickness 18. The distance 100 is relatively constant because the thickness 18 of the sheet material 12 is relatively constant. However, as the weld 20 passes over the support roller 14, the thickened portion 22 causes the second side 26 to move closer to the sensor 16, thereby reducing the distance 100. The differentiator circuit 42 uses this dynamic measurement to produce the rate of change signal.

While specific methods and apparatus have been disclosed in the preceding description, it should be understood that these specifics have been given for the purpose of disclosing the principles of the present invention and that many variations thereof will become apparent to those who are versed in the art. Therefore, the scope of the present invention is to be determined by the appended claims.

Industrial Applicability

The present invention is applicable for converting surface irregularities of elongated pieces of material, whether in sheets, strips, bars, or other shapes, and whether the material is magnetic, nonmagnetic, metallic or nonmetallic, into rate of change signals. The present invention is particularly applicable for locating welds or other types of junctures in materials of the classes described.

What is claimed is:

1. A non-contact method for detecting weld junctures in a steel sheet, said weld junctures being defined by areas of differing sheet thickness, which method comprises:

providing a support surface;

providing an inductive sensor disposed at a fixed distance from said support surface;

transporting said sheet over said support surface such that a first surface of said sheet faces and abuttingly engages said support surface and remains at a constant distance from said sensor and such that an opposing second surface of said sheet faces said sensor;

producing a weld detection signal that is a function of changes in the thickness of said sheet by obtaining from said inductive sensor a varying electrical signal whose variations are a function of variations in said thickness of said sheet and differentiating said varying electrical signal with respect to time, thereby generating said weld detection signal;

determining an allowable weld detection signal based on acceptable variations in the thickness of said sheet; and comparing said produced weld detection signal with said allowable weld detection signal.

2. A method for detecting weld junctures in a sheet constructed of magnetic material, said weld juncture being defined by areas of differing sheet thickness, which method comprises:

transporting said sheet material at a given velocity while supporting a first side of said sheet;

obtaining a varying electrical signal whose variations are a function of variations in the thickness of said sheet by sensing magnetically a second side of said sheet;

developing a rate of change signal by differentiating said varying electrical signal as a function of time;

calculating an allowable rate of change signal using said given velocity and an acceptable variation in sheet thickness in a weld juncture area;

comparing said allowable rate of change signal with said rate of change signal from said developing step;

setting a latch if any difference between the calculated rate of change signal and the allowable rate of change signal is unacceptable;

using said set latch to activate a reject mechanism; and resetting said latch subsequent to said activating of said reject mechanism.

3. A method as claimed in claim 2 in which:

a) said sheet material is magnetic; and b) said obtaining step comprises magnetically varying an electrical signal as a function of a distance between a sensor and a surface of said sheet material.

4. The method as claimed in claim 1 in which said producing step further comprises:

amplifying said varying electrical signal using both resistive and capacitive feedback.

5. The method as claimed in claim 1 in which said method further comprises:

setting a latch as a function of said comparing step;

using said set latch to activate a reject mechanism; and resetting said latch subsequent to said activating of said reject mechanism.

6. The method as claimed in claim 1 in which said producing step comprises supporting said first surface of said sheet upon said support surface and sensing the side opposing second surface of said sheet; and said method further comprises setting a latch as a function of said comparing step, using said set latch to activate a reject mechanism, and resetting said latch subsequent to said activating of said reject mechanism.

7. The method as claimed in claim 2 in which said differentiating of said developing step comprises amplifying said varying electrical signal using both resistive and capacitive feedback, and in which said obtaining step comprises supporting one side of said sheet material and measuring said varying electrical signal as a function of varying positions of the opposing second side of said sheet material in relation to said supporting step.

8. Apparatus for detecting a weld juncture in a sheet material that is being transported at a given velocity, said weld juncture being defined by an area of differing thickness, which apparatus comprises:

means for producing a rate of change signal that is a function of changes in the thickness of said sheet material and said given velocity including sensor means for obtaining a varying signal that is a function of said changes in said thickness of said sheet material and differentiator means operatively connected to said sensor means for differentiating said varying signal with respect to said given velocity; and a comparator operatively connected to said producing means for comparing said rate of change signal with a calculated allowable rate of change signal, said differentiating means comprising a first operational amplifier for amplifying said varying signal;

a first resistor operatively connecting an output of said first operational amplifier to an input thereof; and a first capacitor operatively connecting said output of said first operational amplifier to said input thereof.

9. Apparatus for detecting a weld juncture in a sheet material that is being transported at a high-speed velocity of approximately 600 feet per minute, said weld juncture being defined by an area of differing sheet thickness, which apparatus comprises:

an inductive sensor for producing a varying signal that is a function of changes in the thickness of said sheet material and its velocity of approximately 600 feet per minute;

a support surface disposed a fixed distance from said sensor over which said sheet is transported;

a differentiator operatively connected to said sensor for differentiating said varying signal as a function of time; and a comparator operatively connected to said differentiator for comparing said differentiated signal with an allowable value.

10. Apparatus as claimed in claim 9 in which said differentiator comprises:

an operational amplifier;

a resistor operatively connecting an output of said operational amplifier to an input thereof; and a capacitor operatively connecting said output of said operational amplifier to said input thereof.

11. The apparatus as claimed in claim 8 wherein said first capacitor provides noise filtering, and wherein said differentiating means further includes:

a second operational amplifier having an input that is capacitively connected to said output of said first operational amplifier;

a second resistor operatively connecting an output of said second operational amplifier to said input thereof; and a second capacitor operatively connecting said output of said second operational amplifier to said input thereof.

12. The apparatus as claimed in claim 9 in which said differentiator comprises:

a first operational amplifier operatively connected to said sensor for amplifying said varying signal;

a first capacitor operatively connected to an input and to an output of said first operational amplifier for providing noise filtering;

a second operational amplifier having an input capacitively connected to said output of said first operational amplifier;

a second resistor operatively connecting an output of said second operational amplifier to said input thereof; and a second capacitor operatively connecting said output of said second operational amplifier to said input thereof.

13. The apparatus as claimed in claim 8 further comprising a latch operatively connected to said comparator; and said latch comprises means for electronically resetting said latch.

14. The apparatus as claimed in claim 8 in which said differentiating means further comprises the first operational amplifier being operatively connected to an inductive sensor, a second operational amplifier having an input that is capacitively connected to said output of said first operational amplifier, a second resistor operatively connecting an output of said second operational amplifier to said input thereof, and a second capacitor operatively connecting said output of said second operational amplifier to said input thereof; and said apparatus further comprises an electronic latch operatively connected to said comparator; and said latch including means for electronically resetting said latch.

15. The apparatus as claimed in claim 9 in which said differentiator comprises a first operational amplifier operatively connected to said inductive sensor, a first capacitor operatively connected to an input and to an output of said first operational amplifier, a second operational amplifier having an input capacitively connected to said output of said first operational amplifier, a second resistor operatively connecting an output of said second operational amplifier to said input thereof, and a second capacitor operatively connecting said output of said second operational amplifier to said input thereof.

* * * * *

UNITED STATES PATENT AND TRADEMARK OFFICE
CERTIFICATE OF CORRECTION

PATENT NO. : 5,493,221
DATED :
INVENTOR(S) : February 20, 1996

Ronald D. Wertz

It is certified that error appears in the above-indentified patent and that said Letters Patent is hereby corrected as shown below:

In Col. 2, line 52, after the word "function", change "or" to --of--.

In Col. 3, line 43, before the word "occurring", change "(0.0381" to --(0.0381 mm)--.

In Col. 3, line 65, change "amplifier 60" to --amplifier 50--.

Signed and Sealed this

Second Day of July, 1996

Attest:

BRUCE LEHMAN

Attesting Officer

Commissioner of Patents and Trademarks